United States Patent
Jones et al.

[11] Patent Number: 6,018,983
[45] Date of Patent: Feb. 1, 2000

[54] METHOD AND APPARATUS FOR MATCHING REFRIGERANTS

[75] Inventors: Barbara L. Jones; Paul Smith; Stephen J. Davis, all of Norfolk, United Kingdom

[73] Assignee: Sun Electric U.K. Limited, King's Lynn, United Kingdom

[21] Appl. No.: 09/067,049

[22] Filed: Apr. 27, 1998

[30] Foreign Application Priority Data

May 1, 1997 [GB] United Kingdom .................. 9708778

[51] Int. Cl.[7] ........................... F25B 43/02; F25B 49/02; G01N 1/42; G01N 7/00

[52] U.S. Cl. ................... 73/23.2; 73/61.75; 73/61.48; 73/64.56; 436/181; 250/343; 62/127; 422/68.1

[58] Field of Search ................. 73/23.2, 64.56, 73/61.48, 31.05, 61.75; 422/82.09, 68.1; 356/70, 434; 338/34; 436/181, 171; 324/698, 693; 62/127, 149; 250/341.8, 343, 301; 128/203.12, 204.22

[56] References Cited

U.S. PATENT DOCUMENTS

| | | | |
|---|---|---|---|
| 4,008,388 | 2/1977 | McLafferty et al. | 235/151.35 |
| 4,498,305 | 2/1985 | Bzdula | 62/84 |
| 4,530,233 | 7/1985 | Kadi | 73/23 |
| 4,803,843 | 2/1989 | Otto | 62/85 |
| 4,959,965 | 10/1990 | Browne et al. | 62/129 |
| 5,071,768 | 12/1991 | Klodowski | 436/39 |
| 5,158,747 | 10/1992 | Manz et al. | 422/98 |
| 5,170,634 | 12/1992 | Squires | 62/126 |
| 5,237,873 | 8/1993 | Eichenlaub | 73/597 |
| 5,272,907 | 12/1993 | Hakala | 73/23.2 |
| 5,290,516 | 3/1994 | Greco et al. | 422/57 |
| 5,293,771 | 3/1994 | Ridenour | 73/40 |
| 5,295,360 | 3/1994 | Olds et al. | 62/127 |
| 5,296,843 | 3/1994 | Wohlstein et al. | 340/603 |
| 5,345,774 | 9/1994 | Mount | 62/127 |
| 5,363,661 | 11/1994 | Condit et al. | 62/77 |
| 5,371,019 | 12/1994 | Manz et al. | 436/126 |
| 5,372,785 | 12/1994 | Johnson et al. | 422/90 |
| 5,392,639 | 2/1995 | Manz | 73/61.76 |
| 5,410,887 | 5/1995 | Urata et al. | 62/129 |
| 5,419,177 | 5/1995 | Pastorello | 73/23.4 |
| 5,457,528 | 10/1995 | Tobias | 356/300 |
| 5,469,714 | 11/1995 | Manz et al. | 62/125 |
| 5,481,476 | 1/1996 | Windig | 364/498 |
| 5,514,595 | 5/1996 | Olds et al. | 436/126 |
| 5,524,477 | 6/1996 | Wajid | 73/24.05 |
| 5,528,924 | 6/1996 | Wajid et al. | 73/24.06 |
| 5,569,838 | 10/1996 | Broedel et al. | 73/23.31 |
| 5,597,533 | 1/1997 | Olds et al. | 422/68.1 |
| 5,610,398 | 3/1997 | Anderson et al. | 250/339.12 |
| 5,644,069 | 7/1997 | Liu et al. | 73/23.2 |
| 5,682,231 | 10/1997 | Holsen | 356/70 |
| 5,817,921 | 10/1998 | Tom et al. | 73/24.01 |
| 5,831,144 | 11/1998 | Pastorello | 73/23.2 |

OTHER PUBLICATIONS

W. Gopel, J. Hesse and J.N. Zemel eds.: "Sensors: a comprehensive survey", VCH Weinheim, 1991; W. Gopel and K.–D. Schierbaum: "Electronic Conductance and Capacitance Sensors", vol. 2, Part 1, Ch. 9, pp. 429–431, 434–436 and 446–447 (*).

*Primary Examiner*—Hezron Williams
*Assistant Examiner*—J. David Wiggins
*Attorney, Agent, or Firm*—Emrich & Dithmar

[57] ABSTRACT

Method and apparatus for freon and other refrigerant matching, particularly for servicing of air conditioning systems for automotive applications. The matching process is based upon the comparison of resistance or infrared absorption or other data readings of a gas-sensing resistance or infrared absorption or other transducer applied to the refrigerant fluid under test and corresponding data from reference refrigerants.

18 Claims, 3 Drawing Sheets

METHOD AND APPARATUS FOR MATCHING REFRIGERANTS

BACKGROUND OF THE INVENTION

This invention relates to a method and apparatus for matching refrigerants. An example of the application of the invention is to the matching of freons, but the invention is applicable to other refrigerant fluids including, fluorocarbons generally, hydrofluorocarbons, and aliphatic and aromatic hydrocarbons. A principal application of the invention relates to techniques for the efficient handling of refrigerant fluids, such as those used in automotive air conditioning systems. References hereafter to freons are to be interpreted as including references also to the other refrigerant fluids mentioned above.

In the case of the maintenance/servicing of automotive air conditioning systems and indeed in other refrigeration systems which undergo such maintenance/servicing there is a distinct technical problem in relation to the specific coolant fluids used which arises from the chemical interaction of these fluids when mixed.

The interaction of different coolant fluids such as those designated as R134a and R12 is not an issue which requires detailed exposition in this application. The technical data relating to the interaction is to be found in the published literature on the subject. Suffice it to say that the interaction occurs and its result is a reduction in the cooling effect of the coolant fluid whereby its effectiveness for its intended function is significantly impaired.

More significantly, the interaction effect is not in the nature of a standard chemical interaction between defined molecular proportions of the two ingredients leading to a defined product which, when produced effectively exhausts the supplies of the reactants. The interaction is more in the nature of an initiation reaction which requires only a modest quantity of one of the reacting freons to commence a continuing reaction with the other. It is not known whether this mechanism involves the production of free radicals but it suffices to say that the consequence of this reaction initiation possibility is the need for scrupulous monitoring by servicing facilities of freon types being handled at any given time so as to avoid admixture. It will be readily appreciated that even a single error in freon identification when pumping out the fluid from a given system undergoing maintenance could lead to the contamination of large numbers of other systems which are subsequently refilled with fluid from a reservoir containing even a small quantity of the mis-identified freon. Such a situation could lead to very substantial costs for repeat servicing of large numbers of motor vehicles.

More specifically, as with all air conditioning systems, an automotive air conditioning unit requires periodic preventative servicing in order to maintain its effectiveness. Furthermore, as faults occur, it is necessary to investigate and effect repairs. In either case the procedure requires that the freon or other gas be removed from the air conditioning unit's reservoir and stored in the service equipment while the integrity of the air conditioning unit is determined. The reclaim process is important because it involves the filtration and dehumidification of the freon.

Likewise, the known different types of freon, such as R12 and R134a, when cross-contaminated produce degradation of the freon concerned. More importantly the air conditioning unit and/or service reclaim unit concerned is itself effectively degraded and incapacitated, thereby, leading to costly servicing work. Moreover, contamination of the service equipment may lead to further cross-contamination of other air conditioning units that are subsequently serviced. This could leave the garage auto AC servicing or service-provider liable for the repairs.

SUMMARY OF THE INVENTION

Accordingly, we have identified a substantial need for a simple and cost-effective system for matching of refrigerants during automotive servicing routines so as to avoid or minimize the risks of the contamination and other problems identified above. Certain aspects of the invention go somewhat wider than this, as identified above, and the invention seeks to provide improvements generally in relation to such systems also. In an embodiment, the important step is provided of determining the type of freon present in the vehicle's air conditioning unit and/or ensuring that it matches the freon used in the service reclaim unit, and likewise that even if it is the same freon, that it has not been previously contaminated. The embodiments even enable an approach to the further step of matching contaminant(s) for identified refrigerant(s) utilizing a data base of corresponding contaminant data. This approach is particularly applicable to the use of infrared absorption analysis in which the absorption spectra are readily interpreted on a spectrum-profile basis, whereby standard reference data on typical contaminants enables relatively direct and positive identification of refrigerants and corresponding contaminants.

According to the invention there is provided a method and apparatus for determining a characteristic of a refrigerant fluid, or like fluid, in admixture with air or otherwise, for matching purposes.

The principle of operation of the embodiments provides a device which is used to assess a relevant characteristic of a sample of freon or other refrigerant. Typically, the characteristic assessed will be sensed by an electrical resistance transducer, but other characteristics such as infrared absorption may be used. Appropriate transducer means may be employed for the purpose, such as a Figaro-type (originating from the well known Figaro corporation) gas-sensing resistance transducer or suitable infrared absorption apparatus. In the embodiment the apparatus tests a sample of freon taken from an automotive air conditioning unit to determine whether the sample is predominantly pure and of the same molecular type and configuration as a known pure sample. The invention is based upon our discovery that, in the case of refrigerants such as freons and like fluids, the determination of a characteristic such as those sensed by resistance and/or infrared absorption transducer can be effectively used to determine purity and molecular type and configuration, by comparison with a known pure sample of the freon. Thus a servicing engineer can determine whether a freon removed from an air conditioning system is of the same type as that used in the service equipment and whether the sample is contaminated, thereby enabling a factually-based decision to be made as to whether to proceed with removal of the freon and storage of same.

In an embodiment of the invention the method and apparatus include the step of subjecting the refrigerant fluid to analysis by a gas-sensing resistance (or infrared absorption) transducer and obtaining a signal or reading from the transducer which is indicative of a characteristic of the presence of a fluorocarbon refrigerant fluid. The method and apparatus further comprises the step of using the signal from the transducer in order to make a determination of the matching status of a first such refrigerant fluid with respect to a second such fluid, or even with respect to data thereon.

In the embodiment, the step of using the signal or reading from the transducer comprises causing comparator means to compare the signal or reading from the gas-sensing resistance or infrared absorption transducer from a first refrigerant fluid with at least one signal or reading relating to a second refrigerant fluid, and to make the matching determination accordingly, and to provide a visible or audible or other signal indicative thereof accordingly.

It is noteworthy that in at least the resistance transducer embodiment, the method further comprises the step of controlling or establishing the partial pressure of the refrigerant fluid, under test, at the time of obtaining the signal or reading from the transducer, and making the said comparison of that signal or reading from the gas-sensing resistance transducer with the signal or reading relating to the refrigerant fluid accordingly.

Certain features of the invention may be attained by providing apparatus for determining whether a first refrigerant fluid matches a second refrigerant fluid comprising: a fluid sensing transducer disposed at a sensing location and responsive to an incident refrigerant fluid for generating an output signal indicative of a characteristic of the fluid, inlet apparatus for sequentially admitting first and second refrigerant fluids to the sensing location for exposure to the transducer and causing it to generate first and second output signals respectively corresponding to the first and second refrigerant fluids, and a comparator coupled to the transducer for comparing the first and second output signals and determining whether or not they match.

BRIEF DESCRIPTION OF THE DRAWINGS

An embodiment of the invention will now be described by way of example with reference to the accompanying drawings in which.

DESCRIPTION OF THE PREFERRED EMBODIMENTS

Figure 1:
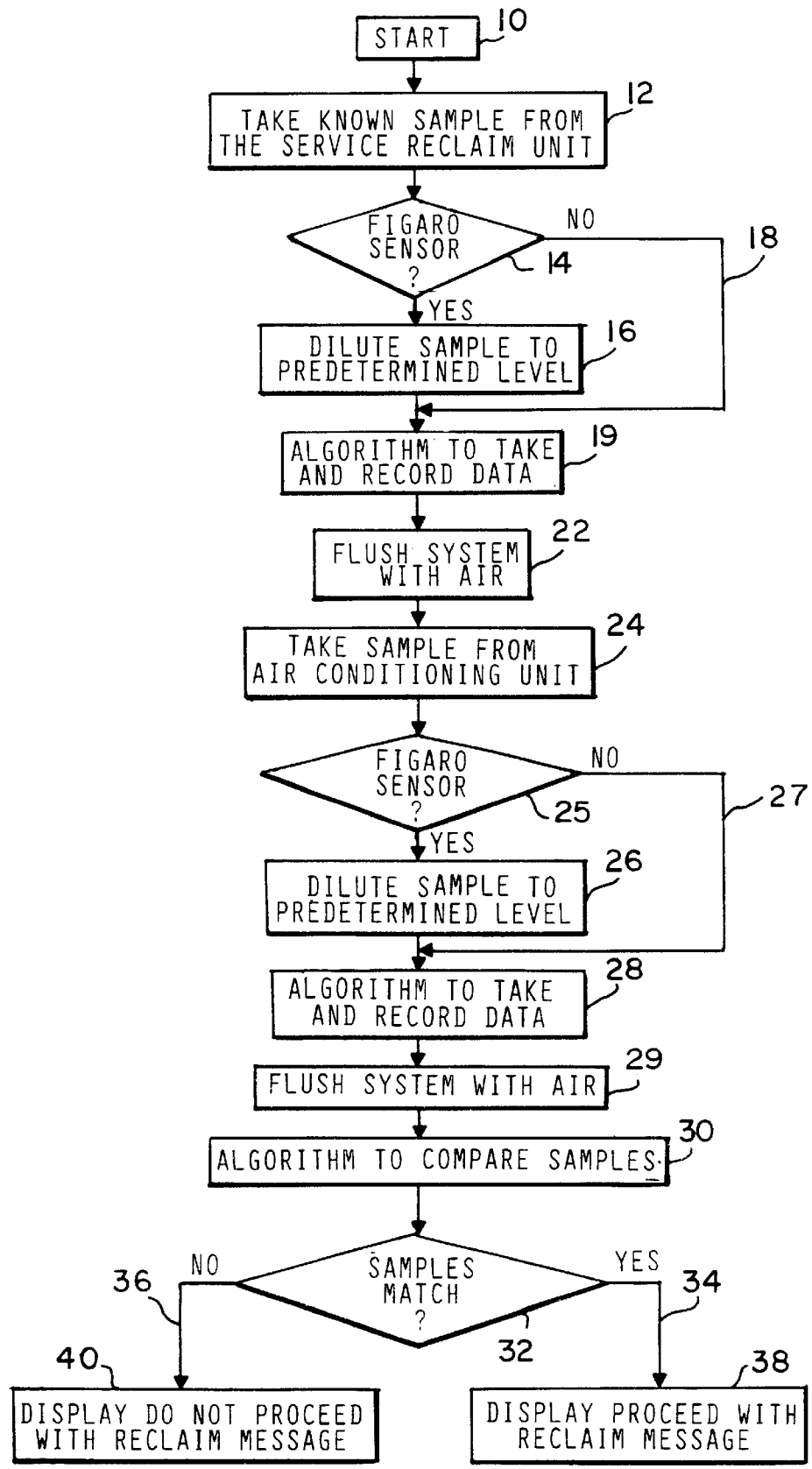
FIG. 1 shows a process flow diagram for a method of determining refrigerant matching status in accordance with the invention.

The invention is based upon our discovery that a valid basis for obtaining an effective indication of the matching of two refrigerant fluids is by comparing data relating to these as obtained from a gas-sensing electrical resistance or infrared absorption (or other) transducer or the like. We have established that the signals or readings obtained from such a transducer when testing, for example, freons R134a and R12, are sufficiently different to enable a valid identification to be made simply on the basis of the resistance or IR absorption or other value produced under test, whereby the comparison step can produce a simple refrigerant match/no match indication for the automotive technician involved. The matching technique also serves for matching contaminated refrigerants due to the characteristic resistance and absorption (and other) values produced which can be stored as data and accessed on a look-up comparison basis.

The method of the invention likewise includes, in the embodiments, the further step of controlling or establishing the partial pressure of the fluorocarbon or other refrigerant fluid under test, whereby the validity of the comparison between the resistance or other values is maintained. It may well be possible to make comparisons of resistance values at significantly differing partial pressures, the values obtained being compared by means of look up tables or corresponding calibration data relating resistance or infrared absorption changes with partial pressure changes.

In the embodiment, a known sample of the freon, for example R134a, used in the service reclaim unit is taken and diluted in air, to a partial pressure corresponding to a dilution in the range 1:500 to 1:5000. The Figaro-type resistance transducer or sensor is subjected to the sample and the resistance of the sensor changes accordingly, within a resistance range of 1 kilohm to 100 kilohms. The system is then flushed with air to remove all traces of the known sample of freon. Then, a similar sample is taken from the vehicle's air conditioning unit and likewise tested for its resistance to determine if the latter is the same as that for the known sample. Differing resistance is indicative of non-matching of the freons. By the use of known resistance bands determined by reference to standard batches of freons R12 and R134a (and these freons contaminated with one of more other freons) there can be established definitive bands of resistance by reference to which the identity of a sample under test can be determined.

In the embodiment utilizing infrared absorption, namely an infrared source and an infrared detector, the principle of operation is much the same as described above in terms of comparing the absorption data of one refrigerant with that of a known refrigerant, or indeed with standardized data for the various available refrigerants, with and without contaminants. This infrared absorption technique has the advantage that the dilution phase of the testing process is not necessary because the infrared absorption apparatus is not subject to poisoning by the freon materials as is the case with Figaro-type sensors.

FIG. 1 shows the sequence of operations including a software algorithm used in the method as applied to an automotive servicing operation carrying out repair or maintenance work on an automotive air conditioning installation.

As shown the method starts at 10 and proceeds at 12 with the taking of a known sample of freon from the service reclaim unit at the automotive service station. That is to say, a sample is taken from the service, station's freon processing apparatus in order to establish the relevant and characteristic data for matching with a sample from the air conditioning unit to be serviced. While the sample from the service reclaim unit is typically known, that is not critical to the fundamental aspect of the invention.

Figure 2:
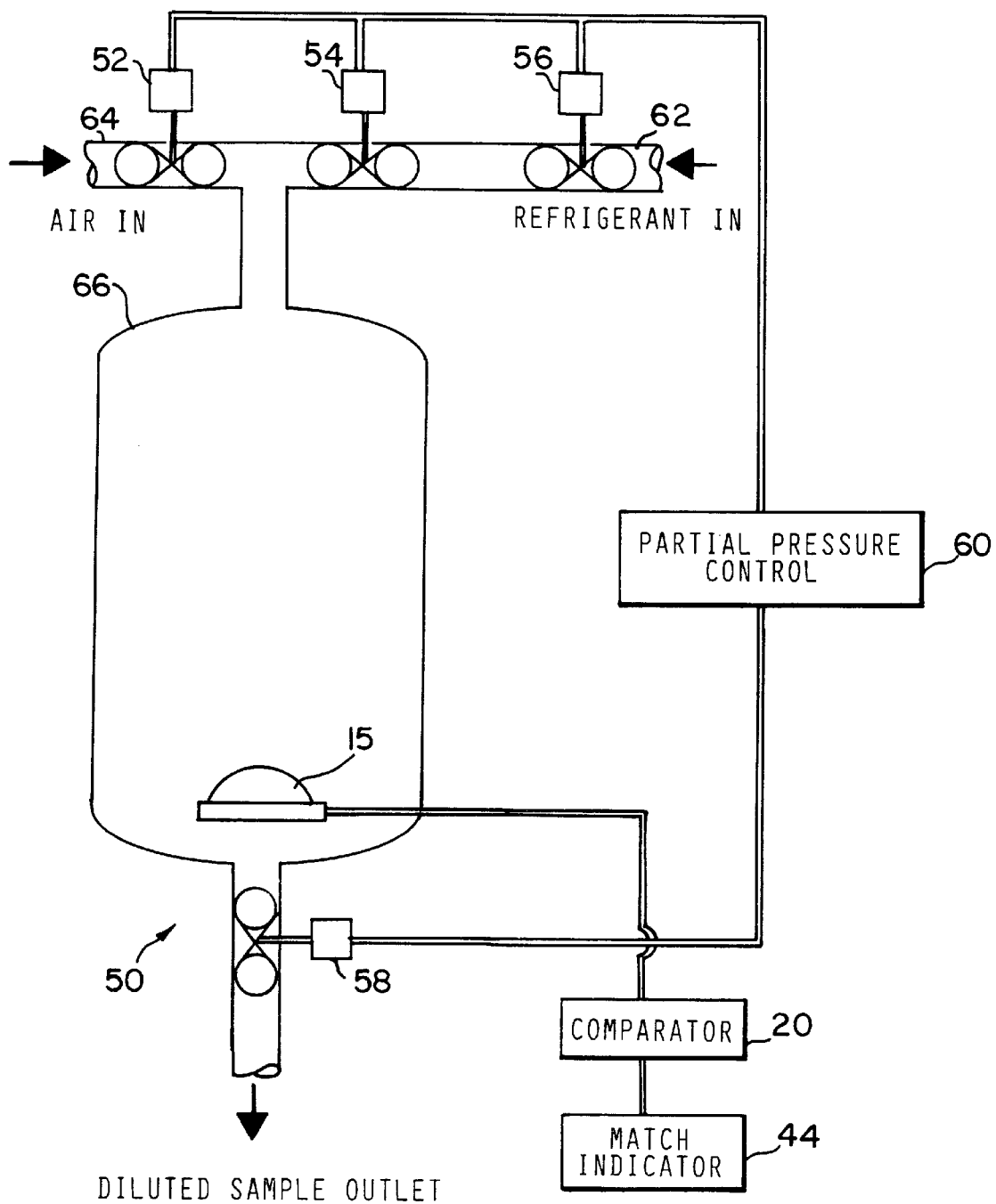
FIG. 2 shows a schematic representation of apparatus utilized in carrying out the process of FIG. 1 with a resistance sensor.

Next, the method checks at 14 to determine if the fluid sensor, used is a resistance-type sensor, such as the Figaro sensor 15 provided in the apparatus as shown in FIG. 2. If so, the freon sample is diluted at 16 with air to a dilution level such as to avoid poisoning the Figaro sensor. Typically this will be at a dilution in the range of 1:500 to 1:5000. If the sensor is not a Figaro sensor (such as an IR absorption sensor), the dilution step is bypassed at 18. The, at 19, data from the sensor is applied to a comparator 20 (FIG. 2) which may include a suitable microprocessor and associated memory, where an algorithm processes the data and stores the result.

Then, at 22 the system is flushed with air and a sample from the automotive air conditioning unit is taken at 24 and caused to enter the apparatus, preferably at a controlled partial pressure. The method again checks at 25 to see if a Figaro sensor is used and, if so, dilutes the sample at 26 to a predetermined level, and if not, bypasses the dilution step at 27. The data from the sensor is then taken and recorded at 28. The system is then preferably flushed with air at 29 and the stored data is processed by the comparator 20 at 30, including the step of comparing the values for the sample from the service reclaim unit and the sample from the air conditioning unit. The algorithm provide a match/ mismatch step at 32 and the resulting match/mismatch signals 34 or 36 are displayed at 38 and 40 on match indicator 44 (FIG. 2).

FIG. 2 shows the corresponding hardware or apparatus 50 including the above-mentioned Figaro sensor 15 and comparator 20 and match indicator 44. Output signals from the sensor 15 are stored and compared in the comparator 20, as described above.

Apparatus 50 further comprises inlet valves 52, 54 and 56 and a diluted sample outlet valve 58 under the control of a partial pressure control system 60, whereby freon from a refrigerant inlet 62 and air from an air inlet 64 are mixed in known volumes in dilution/measurement chamber 66 of known volume in which is also located Figaro sensor 14. The partial pressure control 60 may be controlled by the same processor associated with the comparator 20. The refrigerant inlet valves 54 and 56 are preferably in an inlet conduit 55 having a known volume to facilitate measuring the refrigerant volume.

Use of the apparatus has already been described and it is believed that no further details of operation are required by the skilled person.

Figure 3:
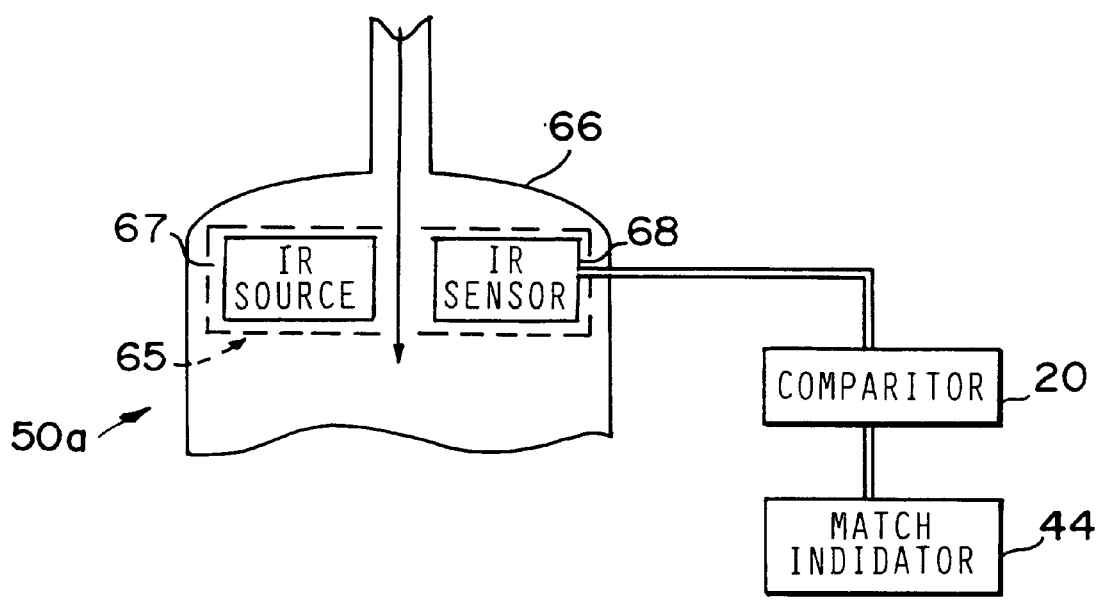
FIG. 3 shows a schematic representation of a portion of apparatus used in carrying out the process of FIG. 1 with an infrared absorption sensor.

An embodiment 50A shown in FIG. 3 employs (in place of the transducer in the form of Figaro sensor) an infrared sensor or transducer, but is otherwise constructed as described above. Specifically, an IR absorption transducer 65 is disposed in the chamber 66 and includes a IR source 67 and an IR sensor 68, for detecting the IR absorption characteristics refrigerant fluid in a known manner. The sensor 68 produces output signals which are stored and compared in the comparator 20, match/mismatch indications being given by the indicator 44. Operation is otherwise generally as described above.

Among other modifications which could be used in the above embodiments without departing from the scope of the invention as described in the claims are the use of alternative refrigerant fluids and alternative transducers or sensors accordingly, which are responsive to other characteristics of the fluids to be tested. Of course, considerable variation of the apparatus for controlling partial pressure can be provided readily. Admixture with air is not necessary for infrared or some other sensing techniques. Likewise, various approaches to the display of results can be adopted. At a minimum the user should preferably know whether a match or mismatch has been obtained, and such can be indicated in a variety of ways. Of course, the apparatus may be calibrated in various ways, including positive identification of refrigerant types in accordance with match/mismatch data obtained in respect of stored data relating to predetermined data values.

While particular embodiments of the present invention have been shown and described, it will be obvious to those skilled in the art that changes and modifications may be made without departing from the invent on in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for determining whether a first refrigerant fluid matches second refrigerant fluid comprising:

a fluid sensing transducer disposed at a sensing location and responsive to an incident refrigerant fluid for generating an output signal indicative of a characteristic of the incident refrigerant fluid, inlet apparatus for sequentially admitting first and second refrigerant fluids to the sensing location for exposure to the transducer and causing it to generate first and second output signals respectively corresponding to the first and second refrigerant fluids, and a comparator coupled to the transducer for comparing the first and second output signals and determining whether or not they match.

2. The apparatus of claim 1, wherein said transducer is a gas-sensing transducer and each of said first and second fluids is a refrigerant gas.

3. The apparatus of claim 1, wherein said transducer includes infrared absorption apparatus.

4. The apparatus of claim 2, wherein said inlet apparatus includes a refrigerant inlet conduit and an air inlet conduit and a mixing chamber communicating with said conduits for diluting the refrigerant fluid to produce first and second diluted refrigerant gases.

5. The apparatus of claim 4, wherein said inlet apparatus includes control valves for controlling partial pressure of the first and second diluted refrigerant gases.

6. The apparatus of claim 5, and further comprising a control unit coupled to said valves for equalizing the partial pressures of the diluted first and second refrigerant gases as exposed to the transducer.

7. The apparatus of claim 5, wherein said transducer is disposed in said mixing chamber.

8. The apparatus of claim 1, wherein said transducer is a resistance transducer and said output signals are indicative of the electrical resistance of the transducer in response to the first and second refrigerant fluids.

9. Apparatus for identifying a refrigerant fluid comprising: a fluid sensing electrical resistance transducer responsive to an incident fluid for generating an output signal indicative of electrical resistance of the transducer, and a comparator coupled to the transducer and responsive to the output signal for comparing it to electrical resistance transducer characteristics associated with a reference fluid;

and further comprising an inlet apparatus that includes a refrigerant inlet conduit and an air inlet conduit and a mixing chamber communicating with said conduits for diluting the refrigerant fluid and attaining a certain partial pressure of the diluted refrigerant gas, where said electrical resistance transducer is disposed within said mixing chamber.

10. The apparatus of claim 9, wherein said inlet apparatus includes control valves for controlling the partial pressure of the diluted refrigerant gas.

11. The apparatus of claim 10, wherein a control unit coupled to said valves for equalizing the partial pressures of the dilute first and second refrigerant gases as exposed to the transducer.

12. A method for determining whether a first refrigerant fluid matches a second refrigerant fluid comprising:

subjecting the firs refrigerant fluid to analysis by a transducer and obtaining a first signal from the transducer indicative of a characteristic of the first refrigerant fluid, subjecting the second refrigerant fluid to analysis by the transducer and obtaining a second signal from the transducer indicative of a characteristic of the second refrigerant fluid, and comparing the first and second signals to determine whether or not the first and second fluids match.

13. The method of claim 12, wherein said transducer is a gas-sensing transducer and each of said first and second fluids is a refrigerant gas.

14. The method of claim 13, and further comprising diluting the refrigerant fluid with air before exposure to the transducer.

15. The method of claim 14, wherein the transducer is subjected to the first and second fluids at substantially equal partial pressures.

16. The method of claim 12, wherein the first and second fluids are exposed to a resistance transducer for generating an output signal indicative of electrical resistance of the transducer.

17. The method of claim 12, wherein the fluids are exposed to an infrared absorption transducer.

18. The method of claim 12, wherein the first and second fluids are exposed sequentially to the transducer, and further comprising flushing the transducer with air between exposures to the two fluids.

* * * * *

UNITED STATES PATENT AND TRADEMARK OFFICE
CERTIFICATE OF CORRECTION

PATENT NO : 6,018,983

DATED : Feb. 1, 2000

INVENTOR(S) : Barbara L. Jones et al.

It is certified that error(s) appear in the above-identified patent and that said Letters Patent are hereby corrected as shown below:

Column 6, line 7, immediately after "matches" insert --a--.
Column 6, lines 50 and 51, cancel "transducer characteristics associated with a reference" and insert
    --characteristics of a reference--
Column 7, line 1, replace "firs" with --first--

Signed and Sealed this

Tenth Day of April, 2001

Attest:

NICHOLAS P. GODICI

Attesting Officer

Acting Director of the United States Patent and Trademark Office